US00PP29241P3

(12) United States Plant Patent
Probasco et al.

(10) Patent No.: US PP29,241 P3
(45) Date of Patent: Apr. 17, 2018

(54) HOP PLANT NAMED 'HBC 568'

(50) Latin Name: *Humulus lupulus*
Varietal Denomination: HBC 568

(71) Applicants: Eugene G. Probasco, Yakima, WA (US); Jason Perrault, Toppenish, WA (US)

(72) Inventors: Eugene G. Probasco, Yakima, WA (US); Jason Perrault, Toppenish, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 14/756,968

(22) Filed: Nov. 2, 2015

(65) Prior Publication Data

US 2016/0360663 P1 Dec. 8, 2016

Related U.S. Application Data

(60) Provisional application No. 62/230,413, filed on Jun. 4, 2015.

(51) Int. Cl.
*A01H 5/00* (2006.01)

(52) U.S. Cl.
USPC ..... Plt./236

(58) Field of Classification Search
USPC ..... Plt./236
CPC ..... A01H 5/00
See application file for complete search history.

*Primary Examiner* — Kent L Bell
(74) *Attorney, Agent, or Firm* — Svendsen Legal, LLC

(57) ABSTRACT

A new hop plant named 'HBC 568' is disclosed. The cones of 'HBC 568' mature in September. 'HBC 568' is used for its aromatic quality.

4 Drawing Sheets

Genus and species: *Humulus lupulus*.
Variety denomination: 'HBC 568'.

STATEMENT REGARDING FEDERALLY SPONSORED RESEARCH OR DEVELOPMENT

None

BACKGROUND OF THE INVENTION

'HBC 568' is a product of a controlled breeding program carried out by the inventors in the Yakima Valley of Washington State. 'HBC 568' resulted from the cross pollination of 'HBC 364' (unpatented *Humulus lupulus* female plant) and male plant '21-10-21' (unpatented). The cross pollination was made in 2008. The plant was selected and assigned accession number 568 in 2010. At this time, it was asexually reproduced via softwood cuttings in a greenhouse near Toppenish, Wash. Prior to 2014, the original single plant of 'HBC 568' was expanded to multiple plants, which were planted in the area of Toppenish, Wash. By 2014, the plants had been observed and evaluated for several years. Throughout several generations of asexual propagation, 'HBC 568' has been observed to retain its distinctive characteristics and remain true to type. Table 1. below, sets forth some of the distinguishing characteristics of 'HBC 568' as compared to its female parent 'HBC 364', and to the 'Chinook' cultivar as a closely comparable cultivar.

TABLE 1

COMPARISON OF 'HBC 568' TO PARENT PLANT

| | Instant Plant | Mother Plant | Chinook |
|---|---|---|---|
| ID #: | 'HBC 568' | 'HBC 364' | — |
| UV Alpha: | 13.5-16.5% | 15-18% | 11.5-15% |

TABLE 1-continued

COMPARISON OF 'HBC 568' TO PARENT PLANT

| | Instant Plant | Mother Plant | Chinook |
|---|---|---|---|
| UV Beta: | 5.5-6.5% | 5-7% | 3.0-4.0% |
| Alpha:Beta: | 2.5 | 3.0 | 3.8 |
| % Co—H: | 27-31% | 18-20% | 27-31% |
| Matures: | 9/20-10/1 | 9/15-9/25 | 9/10-9/20 |

BRIEF DESCRIPTION OF THE PHOTOGRAPHS

Figure 1:
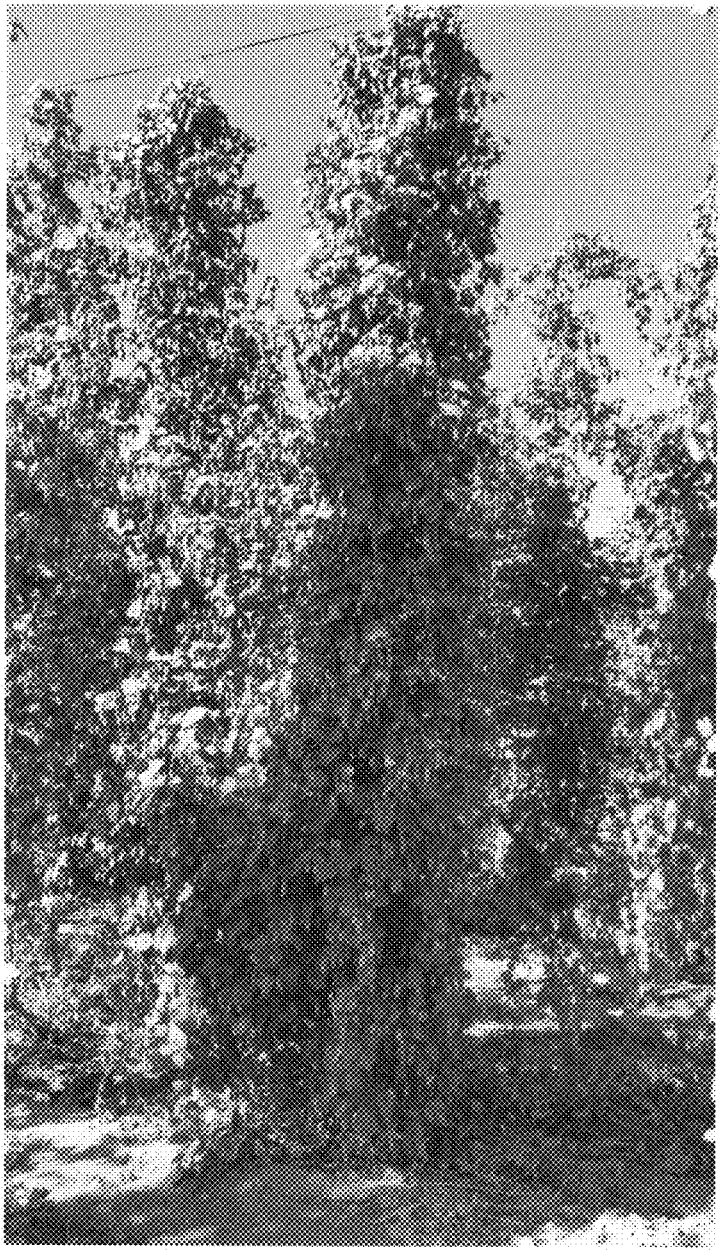
FIG. 1 illustrates a mature 'HBC 568' hop plant grown on a trellis.
Figure 2:
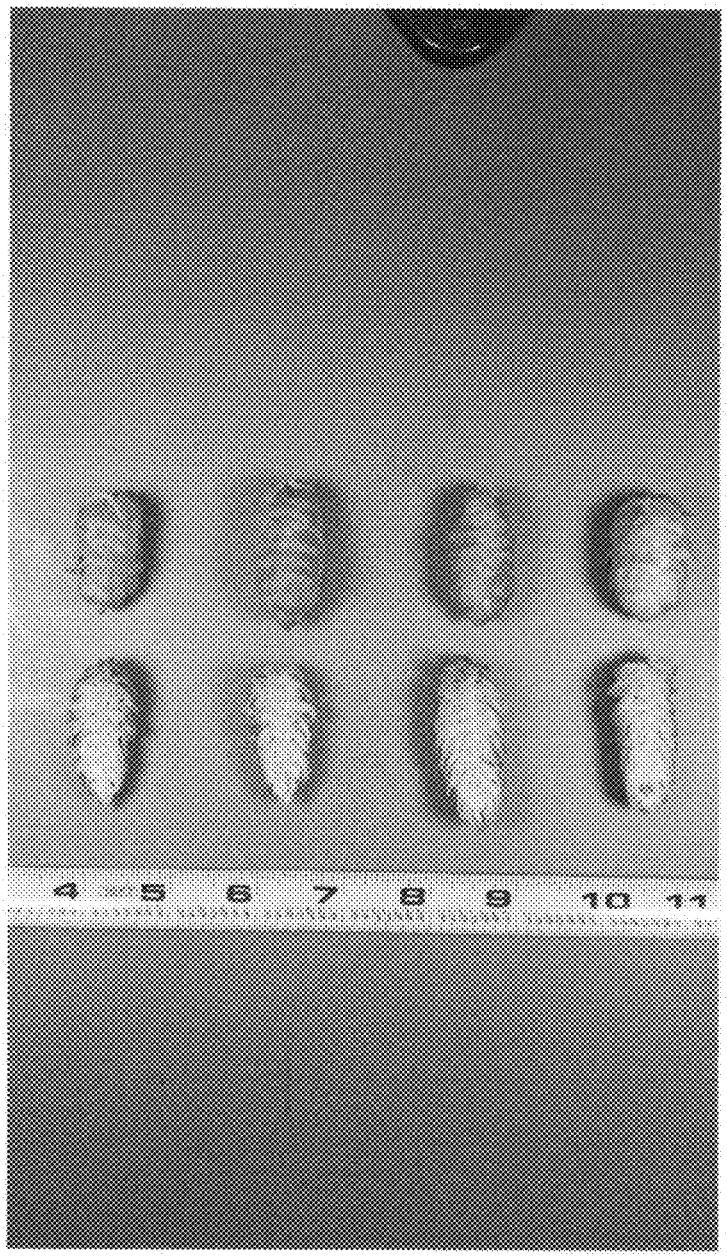
FIG. 2 illustrates whole cones and cross sections of cones of the 'HBC 568' hop plant.
Figure 3:
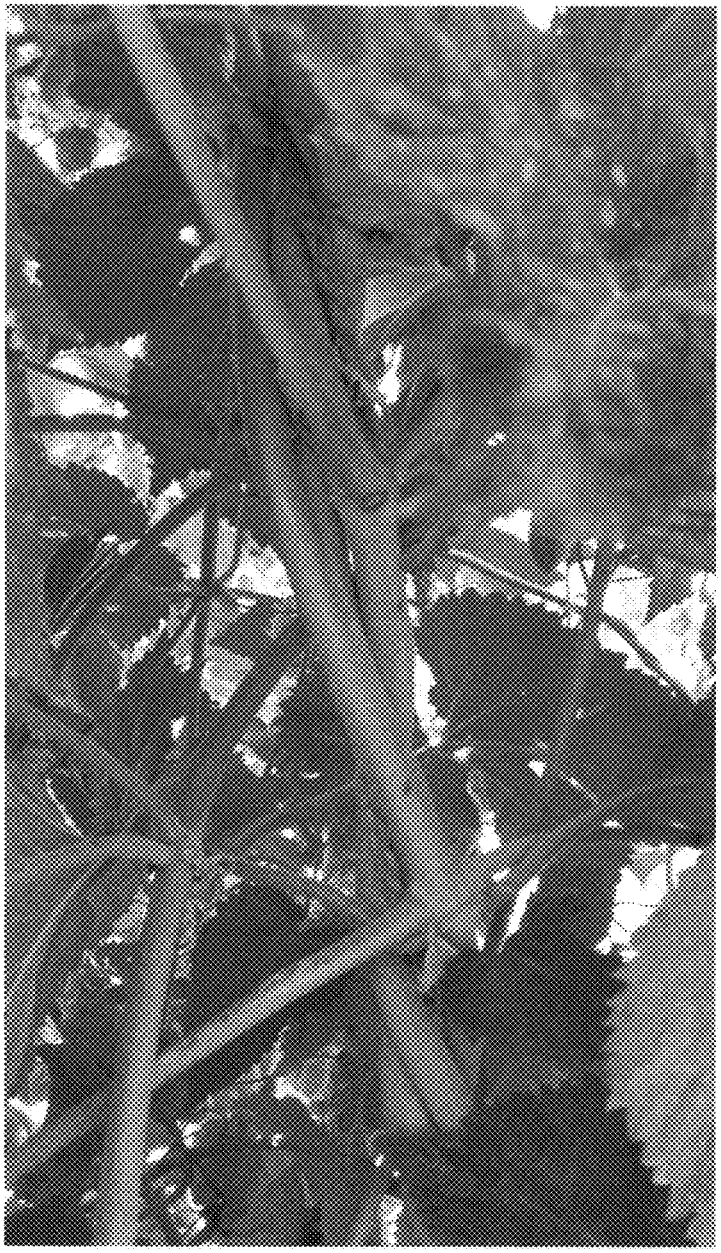
FIG. 3 illustrates the bine of a mature 'HBC 568' hop plant.
Figure 4:
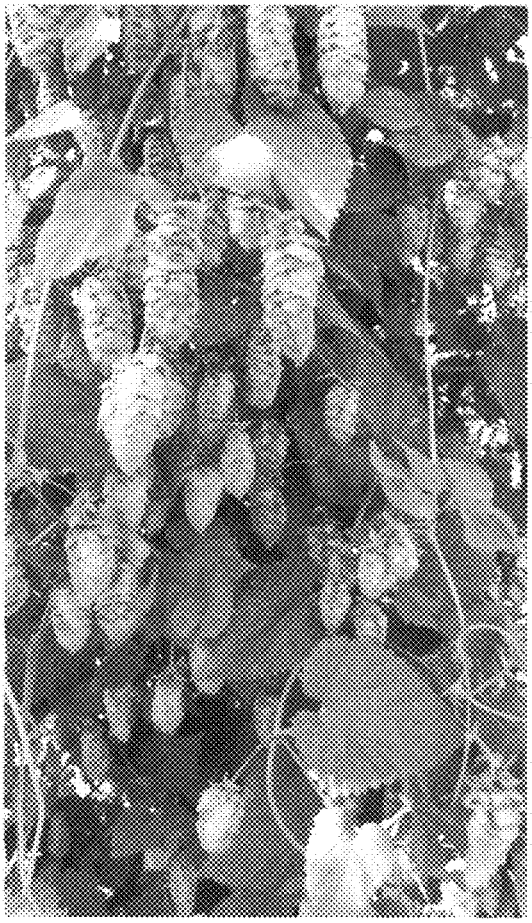
FIG. 4 illustrates the cones and leaves of a mature 'HBC 568' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2013-2014 growing seasons at Toppenish, Wash. It should be understood that the characteristics described will vary somewhat depending upon cultural practices and climatic conditions, and can vary with location and season.

Quantified measurements are expressed as an average of measurements taken from a number of individual plants of the new variety. The measurements of any individual plant or any group of plants, of the new variety may vary from the stated average. All color references are based on The Royal Horticultural Society Colour Chart.

Use: Brewing.

Harvest date: September (during 2013 to 2014 growing seasons at Toppenish, Wash.).

Ploidy: Diploid, 2n=2x.

Disease susceptibility: Moderate resistance to powdery mildew and susceptible to downy mildew.

Crop yield: 2300-2500 lbs per acre.

Plant shape: Climbing bine, columnar growth.

Bine:

*Color*.—Yellow Green 146D.
*Stipule direction*.—Horizontal.
*Stipule average number per bine*.—2 per node.
*Stripe present*.—Yes.
*Stripe color*.—Red Purple 60A.
*Bine diameter*.—11 mm at base and 14 mm at nine feet.
*Bine length*.—19-23 feet when grown under normal commercial conditions on a standard hop trellis.
*Lateral length between internodes*.—190-205 mm.
*Lateral length*.—35 cm.
*Lateral diameter*.—5.2 mm at base and 1.0 mm at terminal end.
*Lateral color*.—Yellow green 145A.

Leaf:

*Arrangement*.—Opposite.
*Shape*.—Palmately lobed.
*Apex*.—Acuminate.
*Base*.—Cordate.
*Mature leaf average length*.—13.0 cm.
*Mature leaf average width*.—18.0 cm.
*Color of mature leaf upper surface*.—Yellow Green 147A.
*Color of mature leaf lower surface*.—Yellow Green 147C.
*Number of lobes*.—1-7.
*Margin*.—Serrate.
*Venation pattern*.—Palmate.
*Vein color*.—Yellow Green 152B.
*Serrations per inch*.—5-6.
*Petiole length*.—8.0-8.5 cm.
*Petiole diameter* (*at the base*).—2.00 mm.
*Petiole color* (*at the base*).—Yellow Green 152B.

Cone:

*Weight*.—1100-1600 mg.
*Shape*.—Ovate.
*Length*.—36 mm.
*Diameter*.—21 mm.
*Pickability*.—Good.

Bract:

*Bract shape*.—Orbicular.
*Length*.—17.5-18.7 mm.
*Width*.—16.5-18.5 mm.
*Bract apex*.—Cuspidate.
*Bract margin*.—Entire.
*Bract base*.—Rounded.
*Bract color upper*.—Yellow Green 145D.
*Bract color lower*.—Green 142C.

Bracteole:

*Bracteole shape*.—Ovate.
*Length*.—14.5-16.6 mm.
*Width*.—9.3-9.4 mm.
*Bracteole color upper*.—Yellow Green 145D.
*Bracteole color lower*.—Yellow Green 145D.

Lupulin glands:

*Lupulin gland shape*.—Pedunculated oblong polyps.
*Lupulin gland average number per cone*.—Moderate.
*Lupulin gland color*.—Yellow 12A.

Analytical characteristics:

*Alpha acid* (*as % of cone weight*).—13.6-16.2%.
*Beta acid* (*as % of cone weight*).—5.3-6.4%.
*Cohumulone* (*as % of alpha acids*).—21-25%.
*Total oil*.—2.1-2.4 mL per 100 g hops.
*Myrcene*.—21-29%
*Humulene*.—6.6-8.9%
*Caryophyllene*.—13.6-17.5%.
*Farnesene*.—0.05-0.18%.
*Linalool*.—0.18-0.2%.
*Storage stability*.—65-75% alpha acids remaining after 6 months storage at room temperature.

What is claimed is:

1. A new and distinct Hop plant as illustrated and described herein.

* * * * *